United States Patent [19]

Ku et al.

[11] Patent Number: 5,864,023

[45] Date of Patent: Jan. 26, 1999

[54] 3'-N'OXIDE, 3'-N-DIMETHYLAMINE, 9-OXIME ERYTHROMYCIN A DERIVATIVES

[75] Inventors: Yi-Yin Ku, Buffalo Grove, Ill.; David A. Riley, Kenosha, Wis.

[73] Assignee: Abbott Laboratories, Abbott Park, Ill.

[21] Appl. No.: 800,009

[22] Filed: Feb. 13, 1997

[51] Int. Cl.⁶ .................................................. C07H 17/08
[52] U.S. Cl. ........................ 536/7.2; 536/7.3; 536/7.4; 536/7.5
[58] Field of Search ............................. 536/7.2, 7.3, 7.4, 536/7.5

[56] References Cited

U.S. PATENT DOCUMENTS

| | | | |
|---|---|---|---|
| 4,331,803 | 5/1982 | Watanabe, et al. | 536/7.2 |
| 4,668,776 | 5/1987 | Yamada, et al. | 536/7.4 |
| 4,670,549 | 6/1987 | Morimoto et al. | 536/7.4 |
| 4,672,109 | 6/1987 | Watanabe et al. | 536/7.2 |
| 4,680,386 | 7/1987 | Morimoto, et al. | 536/7.4 |
| 4,990,602 | 2/1991 | Morimoto, et al. | 536/7.4 |
| 5,274,085 | 12/1993 | Amano, et al. | 536/7.4 |

FOREIGN PATENT DOCUMENTS

| | | |
|---|---|---|
| 0254534 | 1/1988 | European Pat. Off. . |
| 0260938 | 3/1988 | European Pat. Off. . |

OTHER PUBLICATIONS

Technical Information, "Methods of Formulating Controlled Release Products Outside of the Claims of Forest Laboratory Patents".

Green, T. H., et al., "Protective Groups in Organic Synthesis", 2nd Edition, John Wiley & Sons, New York, 1991.

*Primary Examiner*—Scott W. Houtteman
*Attorney, Agent, or Firm*—Mona Anand

[57] ABSTRACT

The disclosed invention relates to novel 3'-N-O, 9-O-oxime protected, 6-O-alkyl erthyromycin derivatives, a process of preparing the same. The invention also relates to a process of preparing 6-O-alkyl erythromycin A by eliminating the 3'-N-oxide group and 9-O-oxime protecting groups and optionally deprotecting the hydroxy groups at the 2'- and 4"-positions under suitable reaction conditions.

12 Claims, No Drawings

3'-N'OXIDE, 3'-N-DIMETHYLAMINE, 9-OXIME ERYTHROMYCIN A DERIVATIVES

TECHNICAL FIELD OF THE INVENTION

The present invention relates to erythromycin derivatives, process of preparing the same and their conversion into 6-O-alkyl erythromycin A. More particularly, the present invention pertains to 3'-N-oxide, 3'-dimethyl-amine, 9-oxime erythromycin A derivatives and their use in the production of 6-O-alkyl erythromycin A.

BACKGROUND OF THE INVENTION

6-O-methylerythromycin A (clarithromycin), shown below, is a potent macrolide antibiotic disclosed in U.S. Pat. No. 4,331,803.

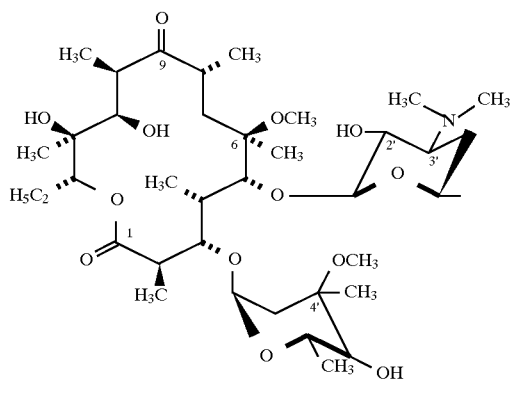

Clarithromycin

In general, the process for making clarithromycin can be thought of as a four-step procedure beginning with erythromycin A as the starting material:

Step 1: optionally convert the 9-oxo group to an oxime;
Step 2: protect the 2' and 4" hydroxyl groups;
Step 3: methylate the 6-hydroxyl group;
Step 4: deprotect at the 2', 4" and 9-positions.

A variety of means for preparing 6-O-methylerythromycin A have been described. 6-O-methylerythromycin A can be prepared by methylating a 2'-O-3'-N-dibenzyloxycarbonyl-des-N-methyl derivative of erythromycin A (U.S. Pat. No. 4,331,803). 6-O-methylerythromycin A can also be made from 9-oxime erythromycin A derivatives (See, e.g., U.S. Pat. Nos. 5,274,085; 4,680,386; 4,668,776; 4,670,549 and 4,672,109 and European Patent Application 0260938 A2).

In those reports relating to 9-oxime erythromycin A derivatives, the oxime is protected during methylation with a 2-alkenyl group (U.S. Pat. Nos. 4,670,549 and 4,668,776), a benzyl or substituted benzyl group (U.S. Pat. Nos. 4,680,386, and 4,670,549) or a moiety selected from the group consisting of lower alkyl, substituted alkyl, lower alkenyl, aryl substituted methyl, substituted oxalkyl, and substituted thiomethyl (U.S. Pat. No. 4,672,109).

There are drawbacks to the existing methods for producing 6-O-methylerythromycin A. By way of example, failure to protect the 2'-OH group leads to undesired methylation of that group. Existing methods for protecting the 2'-OH group are unsatisfactory because those methods also require protection of the 3'-nitrogen. U.S. Pat. No. 4,680,386 discloses protection of the 2'-OH group with a benzyloxy carbonyl moiety. Under such circumstances, however, the 3'-nitrogen also undergoes N-demethylation followed by N-benzyloxy carbonyl formation. This 3'-N-benzyloxy carbonyl group must be deprotected following 6-O-methylation. The 3'-dimethylamino group is regenerated following 6-O-methylation by N-methylation. U.S. Pat. No. 4,670,549 discloses protection of the 2'-OH group as a benzyl or like substituent. Under these circumstances, the 3'-nitrogen group must also be protected as a quaternary salt. This quaternary salt must be removed following 6-O-methylation to regenerate the 3'-dimethyl amino group. By way of further example, the use of benzyloxycarbonyl groups for protection of the 2'-hydroxy group (U.S. Pat. No. 4,331,803) requires large amounts of benzyl chloroformate, which is severely irritating and toxic.

There continues to be a need to provide a rapid, efficient method of producing 6-O-alkylerythromycin compounds that uses mild, neutral synthetic conditions. In particular, it is desirable to provide a process which does not require protection of the 2'-hydroxy group.

SUMMARY OF THE INVENTION

The invention relates to a novel 3'-N-oxide, 3'-N-dimethylamine, 9-oxime, 6-O-alkyl erythromycin A derivatives, to a process for preparing the same, and their use in preparing 6-O-alkyl erythromycin A.

In one aspect, the present invention relates to a compound having the formula:

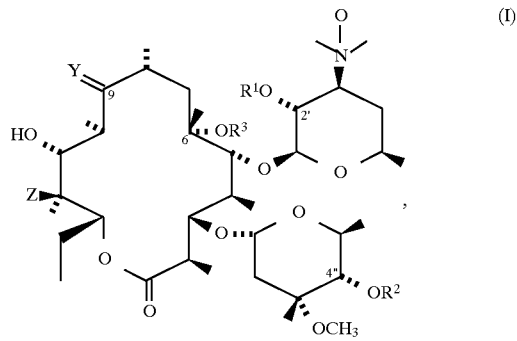

wherein $R^1$ and $R^2$ are independently hydrogen or a hydroxy-protecting group;

$R^3$ is a loweralkyl group;

Y is selected from the group consisting of:
  a) an oxime having the formula: N-O-$R^4$, wherein
     $R^4$ is selected from the group consisting of:
       a loweralkenyl group;
       an alkylaryl group;
       substituted alkylaryl group;
       an aryl(loweralkyl) group, or
       a substituted aryl(loweralkyl) group; or
  b) an oxime having the formula:

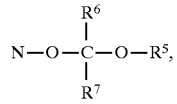

wherein
  $R^5$ is selected from the group consisting of:
    a loweralkyl group,
    a cycloalkyl group,
    a phenyl group,
    an aryl(loweralkyl) group;

or $R^5$ and $R^6$ or $R^5$ and $R^7$ and the atoms to which they are attached are taken together form a 5- to 7-membered ring containing one oxygen atom;

$R^6$ is selected from the group consisting of:
  a loweralkyl group,
  a loweralkoxymethyl group;
  or $R^6$ and $R^5$ and the atoms to which they are attached are taken together form a 5- to 7-membered ring containing one oxygen atom,
  or $R^5$ and $R^6$ and the atoms to which they are attached are taken together form a 5- to 7-membered cycloalkyl group; and $R^7$ is selected from the group consisting of:
  a hydrogen atom,
  a loweralkyl group,
  a phenyl group,
  an aryl(loweralkyl) group;
  or $R^7$ and $R^5$ and the atoms to which they are attached are taken together form a 5- to 7-membered ring containing one oxygen atom;
  or $R^7$ and $R^6$ and the atoms to which they are attached are taken together form a 5- to 7-membered cycloalkyl group;
  with the requirement that only one pair of substituents ($R^5$ and $R^6$), ($R^5$ and $R^7$) or ($R^6$ and $R^7$) may be taken together with the atoms to which they are attached to form a ring as defined above; and Z is hydrogen, hydroxy or protected-hydroxy.

In another aspect, the present invention relates to a process for preparing the compounds of formula (I), comprising the steps of:

a) preparing a 9-O-protected oxime derivative of the compound having the formula:

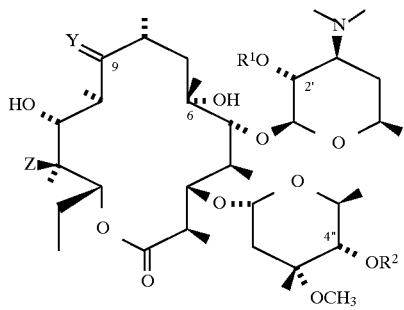

wherein Y, $R^1$, $R^2$, and Z are as defined above; and b) oxidizing the 3'-N of the 9-O-protected oxime derivative to obtain a compound having the formula:

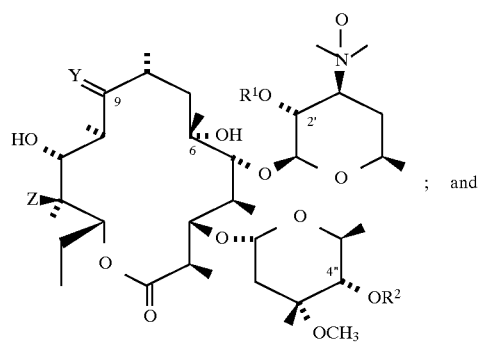

c) alkylating the 6-hydroxy group of the compound of formula (III) with an alkylating agent.

In another aspect, the present invention relates to a process for preparing 6-O-alkyl erythromycin A comprising:

eliminating 3'-N-oxide group, the 9-O-oxime protecting group, and optionally deprotecting the 2'- and 4"- hydroxy groups in the compound of formula (I).

The compounds of the invention are useful key intermediates in the preparation of 6-O-alkyl erythromycin A derivatives. The process of preparing the compounds of the invention and their subsequent conversion into 6-O-alkyl erythromycins provide an efficient process, which eliminates the need for protecting the 2'-OH group, and makes it easy to introduce and remove the N-oxide functionality under mild conditions. The 6-O-alkyl erythromycins are known antibacterial agents as described above.

DETAILED DESCRIPTION OF THE INVENTION

Definitions

A number of defined terms are used herein to designate particular elements of the present invention. When so used, the following meanings are intended:

The term "erythromycin derivatives" refers to erythromycin A having no substituent group or having conventional substituent groups, in organic synthesis, in place of the hydrogen atoms of the 2'-, and 4'-hydroxy groups.

The term "alkyl" refers to saturated, straight- or branched-chain hydrocarbon radicals containing between one and ten carbon atoms including, but not limited to, methyl, ethyl, propyl, isopropyl, n-butyl, tert-butyl and neopentyl.

The term "alkylating reagent" refers to a reagent capable of placing an alkyl group onto a nucleophilic site, including, but not limited to, alkyl halides such as methyl bromide, ethyl bromide, n-propyl bromide, methyl iodide, ethyl iodide, n-propyl bromide; dialkyl sulfates such as dimethyl sulfate, diethyl sulfate, di-n-propyl sulfate; and alkyl or aryl sulfonates such as methyl-p-toluenesulfonate, ethyl methanesulfonate, n-propyl methanesulfonate, and the like.

The term "aryl(loweralkyl)" refers to a loweralkyl radical having appended thereto 1–3 aromatic hydrocarbon groups, as for example benzyl, diphenylbenzyl, trityl and phenylethyl.

The term "aryloxy" refers to an aromatic hydrocarbon radical which is joined to the rest of the molecule via an ether linkage (i.e., through an oxygen atom), as for example phenoxy.

The term "cycloalkyl" refers to a saturated monocyclic hydrocarbon radical having from three to eight carbon atoms in the ring and optionally substituted with between one and three additional radicals selected from among loweralkyl, halo(loweralkyl), loweralkoxy, halogen. Examples of cycloalkyl radicals include, but are not limited to, cyclopropyl, cyclobutyl, cyclopentyl, cyclohexyl, cycloheptyl, 1-fluoro-cyclopropyl, 2-fluorocyclopropyl and 2-aminocyclopropyl.

The term "hydroxy-protecting group" is well-known in the art and refers to substituents on functional hydroxy groups of compounds undergoing chemical transformation which prevent undesired reactions and degradations during a synthesis (see, for example, T. H. Greene and P. G. M. Wuts, Protective Groups in Organic Synthesis, 2nd edition, John Wiley & Sons, New York (1991)). Examples of hydroxy-protecting groups include, but are not limited to, benzyloxycarbonyl, acetyl, or a substituted silyl group of formula $SiR^8R^9R^{10}$, wherein $R^8$, $R^9$ and $R^{10}$ are the same or different and each is a hydrogen atom, a loweralkyl group, a phenyl-substituted alkyl group in which the alkyl moiety has 1 to 3 carbon atoms, a phenyl group, a cycloalkyl group having 5 to 7 carbon atoms, or a loweralkenyl group having 2 to 5 carbon atoms and wherein at least one of $R^8$, $R^9$ and $R^{10}$ is not a hydrogen atom; and the like The term "loweralkenyl" refers to a straight- or branched-chain hydrocarbon radical containing between two and six carbon atoms and possessing at least one carbon-carbon double bond. Examples of loweralkenyl radicals include vinyl, allyl, 2- or 3-butenyl, 2-,3- or 4-pentenyl, 2-,3-,4- or 5-hexenyl and isomeric forms thereof.

The term "loweralkoxy" refers to an loweralkyl radical which is joined to the rest of the molecule via an ether linkage (i.e., through an oxygen atom). Examples of loweralkoxy radicals include, but are not limited to, methoxy and ethyloxy.

The term "loweralkyl" refers to an alkyl radical containing one to six carbon atoms including, but not limited to, methyl, ethyl, propyl, isopropyl, n-butyl, tert-butyl and neopentyl.

The term "alkylaryl" refers to an aryl group having alkyl substituents attached to the aryl group.

The term "substituted alkylaryl" refers to an alkylaryl group as defined above, substituted with substituents such as nitro, alkyl, amino, halo, alkoxy as defined above, and the like.

The term "protected hydroxy" refers to a hydroxy group protected with a hydroxy protecting group, as defined above.

The term "polar aprotic solvent" refers to polar organic solvents lacking an easily removed proton, including, but not limited to, N,N-dimethyl-formamide, dimethyl sulfoxide, N-methyl-2-pyrrolidone, hexamethyl-phosphoric triamide, tetrahydrofuran, 1,2-dimethoxyethane, acetonitrile or ethyl acetate, and the like.

The term "strong alkali metal base" refers to an alkali metal base having a weak conjugate acid, including, but not limited to, sodium hydroxide, potassium hydroxide, sodium hydride, potassium hydride, potassium t-butoxide, and the like.

The term "substituted aryl(loweralkyl)" refers to an aryl (loweralkyl) residue as defined above having between one and three non-hydrogen ring substituents, each independently selected from among halogen, loweralkoxy, loweralkyl, hydroxy-substituted loweralkyl, and (loweralkyl)amino. Examples of substituted aryl (loweralkyl) radicals include 2-fluorophenylmethyl, 4-fluorophenylethyl and 2,4-difluorophenylpropyl.

The process of the invention comprises the steps of converting an erythromycin derivative into a 9-oxime derivative by methods known in the art. For example, the erythromycin derivative is reacted with either hydroxylamine and base, free hydroxylamine in methanol or hydroxylamine and an organic acid (See, e.g., U.S. Pat. No. 5,274,085), the disclosure of which is incorporated herein by reference.

The hydroxy group of the 9-oxime is protected by reaction with a hydroxy protecting group described above by methods known in the art. The hydroxy group of the 9-oxime may also be protected by reaction with a compound of the formula:

$$R^8-\underset{\underset{R^7}{|}}{\overset{\overset{R^6}{|}}{C}}-O-R^5,\qquad (IV)$$

wherein $R^5$, $R^6$, $R^7$ are as defined above, and $R^8$ is a group of formula $-O-R^9$ wherein $R^9$ is an alkyl group having 1 to 6 carbon atoms, in a solvent in the presence of a catalyst with stirring to give a compound of the formula II. In this reaction, the amount of the compound of formula (IV) is 2 to 20 equivalents, preferably 2 to 10 equivalents relative to the 9-oxime erythromycin derivative.

Examples of the compounds of formula (IV) are described in U.S. Pat. No. 4,990,602, which is incorporated herein by reference. Preferably, the 9-O-oxime protecting group is selected from the group consisting of isopropylcyclo-hexyl ketal, 2-chlorobenzyl, trialkylsilyl, acyl and allyl groups.

Examples of the solvent used for the reaction of erythromycin A 9-oxime with the compound of formula IV are dichloromethane, chloroform, tetrahydrofuran (THF), N,N-dimethylformamide, dimethyl sulfoxide, acetone, acetonitrile, nitroethane, toluene and the like. Examples of the catalysts are salts of tert-amines (e.g., pyridine, triethylamine and the like) with hydrochloric acid, sulfonic acid, p-toluenesulfonic acid, formic acid and the like, preferably pyridine hydrochloric and pyridinium p-toluenesulfonate. The amount of the catalyst used from is about 1.5 to about 5 equivalents, preferably from about 1.5 to about 2 equivalents relative to erythromycin A 9-oxime. The reaction temperature is from 0° C. to the reflux temperature of the solvent, but usually the reaction proceeds at room temperature.

The N-oxidation of the 9-O-protected oxime erythromycin derivative is carried out by reacting the 9-O-protected oxime with a suitable oxidizing agent in a suitable solvent. Examples of suitable oxidizing agents include m-chloroperoxybenzoic in methylene chloride, peroxybenzoic acid in benzene, hydrogen peroxide in methanol, t-butylhydroperoxide in the presence of vanadium pentoxide, and calcium carbonate with ozone and the like.

The amount of oxidizing agents varies from 1.0 to 10 equivalents, preferably, from 1.5 to 2 equivalents relative to the erythromycin 9-oxime compound. The reaction temperature is from –20° C. to reflux temperature of the solvent, but usually the reactions are carried out at room temperature for a period of 5 minutes to 48 hours.

The alkylation of the 3'-N-oxide compound so obtained is carried out with an alkylating reagent in presence of a strong alkali metal base, in a suitable stirred or agitated polar aprotic solvent, or a mixture of such polar aprotic solvents maintained at a reaction temperature and for a period of time sufficient to effect alkyation, preferably from –15° C. to room temperature for a period of one to 8 hours. The alkylating agents comprise methyl bromide, ethyl bromide, n-propyl bromide, methyl iodide, ethyl iodide, n-propyl bromide, dimethyl sulfate, diethyl sulfate, di-n-propyl sulfate, methyl-p-toluenesulfonate, ethyl methanesulfonate, and n-propyl methanesulfonate. The amount of alkylating agent used is from 1 to 3 molar equivalents relative to the 3'-N-oxide compound. The alkali metal base is selected from the group consisting of an alkali metal hydride, alkali metal hydroxide or alkali metal alkoxide. Examples of the alkali metal base include sodium and potassium hydride, sodium and potassium hydroxide and potassium t-butoxide. The amount of the base used is usually 1 to 2 equivalents relative to the 3'-N-oxide compound.

The 3'-N-oxide, 6-O-alkyl, 9-O-oxime erythromycin derivative is then reduced to 3'- N-dimethyl, 6-O-alkyl, 9-O-oxime by reaction with a reducing agent in a suitable solvent. The reaction is carried out at a temperature of about 0° C. to about 60° C. for a period from about 1 to about 48 hours. Examples of reducing agents include hydrogen and Raney Nickel in ethanol, hydrogen and platinum oxide, Sodium telerium hydride in ethanol, formic acetic anhydride in methylene chloride, sodium-nickel alloy and potassium hydroxide in methanol, tributyl tin in tetrahydrofuran (THF), samarium iodide in dioxane, hydroxylamine hydrochloride in THF, lithium iodide in dioxane, ferric nitrate, stannic chloride and sodium iodide in acetonitrile, Backer's yeast in water, ferrous sulfate in methanol, zinc in acetic acid and water and the like.

The 9-O-oxime protecting group is easily eliminated to reproduce the 9-keto group by deoximation can be carried out under the conditions as described in Referential Examples 1–3 of U.S. Pat. No. 4,990,602 incorporated herein by reference.

If the compounds of the invention are protected with hydroxy protecting groups at 2'-, and 4"-positions, such hydroxy protecting groups are eliminated under suitable conditions known in the art.

EXAMPLES

The following examples, which are provided for illustration and not limitation of the invention, will serve to further illustrate the process and the advantages of the invention.

Where mixtures of starting material are utilized, the starting material is dissolved in the appropriate solvent and analyzed by HPLC, thus providing an exact estimate of each individual compound. A similar HPLC analysis was performed on the mixtures of products, to provide an exact estimate of each product compound.

Abbreviations

Certain abbreviations are used repeatedly in the specification which follows. These include: DMSO for dimethyl sulfoxide; HPLC for high performance liquid chromatography; IPCH ketal for isopropyl cyclohexyl ketal; TEA for triethylamine; THF for tetrahydrofuran; TMS for trimethylsilyl.

Examples 1–3 describe the preparation of 9-O-protected oxime, 3'-N-O-oxide erythromycin A compounds. The starting materials, 9-O-protected oxime erythromycin A derivatives, in these Examples are prepared by the methods known in the art, see for example, U.S. Pat. No. 4,672,109.

Example 1

Preparation of Erythromycin A Isopropylcyclohexyl Ketal Oxime N-oxide

To a suspension of erythromycin A isopropylcyclohexyl ketal oxime (8.88 g, 10 mmol) in methylene chloride (100 ml) was added 3-chloroperoxy-benzoic acid (3.45 g). The reaction mixture was stirred at room temperature for 2 hours. The solvent was removed under reduced pressure to give a white solid which was suspended in a 20% solution of NaHCO$_3$. The solid was filtered and redissolved in MeOH (100 ml), and it was then precipitated out with 10% K$_2$CO$_3$ solution. The solid was filtered, washed with H$_2$O and dried in a vacuum oven at 40° C. overnight to give 8.1 g of erythromycin A isopropyl-cyclohexyl ketal oxime N-oxide as a white solid. The structure was confirmed by NMR and mass spectra. Mass spectrum (APCI): [M+H]+/z=905, MW=904. 1H NMR (500 MHz, CDCl$_3$); d (ppm)=1.45 (3H, s, 6-CH$_3$), 3.25 (3H, s, O—NCH$_3$), 3.28 (3H, s, O—NCH$_3$), 3.36 (3H, s, 3"-OCH$_3$). 13C NMR (MeOH-d4); d (ppm)= 54.7 (O—NCH$_3$), 57.8 (O—NCH$_3$), 50.1 (3"-OCH$_3$), 76.1 (6-C), 97.8 (1"-C), 103.1 (1'-C), 171.9 (9-C), 177.0 (1-C).

Example 2

Preparation of Erythromycin A 9-O-(2-chlorobenzyl) Oxime

To a cooled (~5° C.) solution of erythromycin A 9-oxime (15 g) in dimethylsulfoxide (25 ml) and tetrahydrofuran (25 ml) was added 2-chloro-benzyl chloride (3.2 g) and 85% KOH (91.5 g). The mixture was stirred at 5~10 ° C. for 3 hours. To the mixture was then added 40% aqueous methylamine solution (5 ml), the mixture was stirred for 10 minutes, water (50 ml) was added. The product was extracted with isopropyl acetate (200 ml). The organic layer was washed with water (2×100 ml), dried over Na$_2$SO$_4$ and concentrated under vacuo to give a white solid, which was triturated with heptane, filtered and dried to give 11 g of erythromycin A 9-O-(2-chlorobenzyl) Oxime as a white solid. The structure was confirmed by NMR and mass spectra. Mass spectrum (CI): [M+H]+/z=873, MW=872. 1H NMR (500 MHz, CDCl$_3$); d (ppm)=2.28 (6H, s, 3'-N—(CH$_3$)$_2$), 3.31 (3H, s, 3"-OCH$_3$), 5.16 (2H, s, —OCH$_2$). 13C NMR (CDCl$_3$); d (ppm)=40.2 (3'-N—(CH$_3$)$_2$), 49.4 (3"-OCH$_3$), 73.0 (-OCH$_2$).

Example 3

Preparation of Erythromycin A 9-O-(2-chlorobenzyl) Oxime N-oxide

To a solution of erythromycin A 9-O-(2-chlorobenzyl) oxime (8.72 g, 10 mmol) in methylene chloride (100 ml) was added 3-chloroperoxybenzoic acid (3.45 g). The reaction mixture was stirred at room temperature for 1/2 hours. The solvent was removed under reduced pressure to give a white solid which was suspended in a 20% solution of NaHCO$_3$. The solid was filtered and redissolved in MeOH (100 ml), and it was then precipitated out with 10% K$_2$CO$_3$ solution. The solid was filtered, washed with H$_2$O and dried in a vacuum oven at 4Pre0 ° C. overnight to give 8.5 g of erythromycin A 9-O-(2-chlorobenzyl) oxime N-oxide. The structure was confirmed by NMR and mass spectra. Mass spectrum (APCI): [M+H]+/z=889, MW=888. 1H NMR (500 MHz, CDCl$_3$); d (ppm)=1.41 (3H, s, 6-CH$_3$), 3.21 (3H, s, O-NCH$_3$), 3.23 (3H,s, O—NCH$_3$), 3.37 (3H, s, 3"-OCH$_3$), 5.16 (2H, s, —OCH$_2$), 7.28~7.48 (4H, m, Ar). 13C NMR (CDCl$_3$); d (ppm)=54.3 (O-NCH$_3$), 58.3 (O-NCH$_3$), 50.1 (3"-OCH$_3$), 75.9(6-C), 97.8 (1"-C), 103.1 (1'-C), 130.2~137.0 (Ar-C), ( 173.0 (9-C), 177.4 (1-C).

Example 4

Preparation of 6-O-Methylerythromycin A Isopropylcyclohexyl Ketal Oxime N-oxide

To an ice-cooled (0°~5° C.) solution of erythromycin A isopropyl-cyclohexyl ketal oxime N-oxide of Example 1 (904 mg, 1 mmol) in a mixture of dimethylsulfoxide and tetrahydrofuran (8 ml, 1:1 mixture) was added potassium hydroxide (87% pure, 225 mg, 3.5 mmol), the reaction mixture was stirred at 1°~5° C. for 20 minutes. Methyl iodide (0.22, 3.5 mmol) was then added. The resulting mixture was stirred at 1°~5° C. for 1.5 hours and was poured into 50 ml of half saturated sodium chloride solution. The product was extracted with ethyl acetate (3×50 ml). The organic layers were separated, combined and washed with saturated sodium chloride solution, it was then dried over Na$_2$SO$_4$ and concentrated under the reduced pressure to give 956 mg of crude 6-O-Methylerythromycin A Isopropylcyclohexyl Ketal Oxime N-oxide as a light yellow solid which was used in the next step without further purification. The structure was confirmed by mass spectra. Mass spectrum (LC-MS): [M+H]+/z=919, MW=918.

Example 5

Preparation of 6-O-Methylerythromycin A 9-O-(2-chlorobenzyl) Oxime N-oxide

To a ice-cooled solution of erythromycin A 9-O-(2-chlorobenzyl) oxime N-oxide obtained above (888 mg, 1 mmol) in a mixture of dimethyl sulfoxide and tetrahydrofuran (8 ml, 1:1 mixture) were added potassium hydroxide (87% pure, 193 mg, 3.0 mmol), the reaction mixture was stirred at 1°~5 ° C. for 35 minutes. Methyl iodide (0.19, 3.0 mmol) was then added. The resulting mixture was stirred at 1~5° C. for 35 minutes and was poured into 50 ml of half saturated sodium chloride solution. The product was extracted with ethyl acetate (3×50 m). The organic layers were separated, combined and washed with saturated sodium chloride solution, it was then dried over $Na_2SO_4$ and concentrated under the reduced pressure to give 860 mg of crude product as a white glassy solid which was used in the next step without further purification. The structure was confirmed by mass spectra. Mass spectrum (LC-MS): [M+H]+/z=903, MW=902.

Example 6

Preparation of 6-O-Methylerythromycin A Isopropylcyclohexyl Ketal Oxime

To a solution of crude 6-O-methylerythromycin A isopropylcyclohexyl ketal oxime N-oxide (1.0 g) in ethanol (30 ml) was added catalyst W4-Raney Ni. The reaction mixture was shaken vigorously at 40° C. for 3.5 hours under 5 psi hydrogen pressure, the mixture was filtered, the catalyst was washed with ethanol. The combined filtrate was concentrated under the reduced pressure to give crude 6-O-methylerythromycin A isopropylcyclohexyl ketal oxime as a glassy solid. The crude product was purified by column chromatography (100: 2:1 chloroform : methanol : triethylamine) to give 438 mg of 6-O-methyl-erythromycin A isopropylcyclohexyl ketal oxime as a white solid. The structure was confirmed by NMR and mass spectra. Mass spectrum (FAB): [M+H]+/z=903, MW=902. 1H NMR (500 MHz, $CDCl_3$); d (ppm)=1.41 (3H, s, 6-$CH_3$), 2.30 (6H, s, 3'-N—$(CH_3)_2$), 3.11 (3H, 6-$OCH_3$), (3.33 (3H, s, 3"-$OCH_3$). 13C NMR ($CDCl_3$); d (ppm)=40.3 (3'-N—$(CH_3)_2$), 49.4 (3"-$OCH_3$), 78.7 (6-C), 96.0 (1"-C), 102.7 (1'-C), 169.8 (9-C), 175.5 (1-C).

Example 7

Preparation of 6-O-Methylerythromycin A 9-O-(2-chlorobenzyl) Oxime

To a solution of 6-O-methylerythromycin A 9-O-(2-chlorobenzyl) oxime N-oxide obtained above (500 mg) in ethanol (30 ml) was added the catalyst W4-Raney Ni. The reaction mixture was shaken vigorously at 40° C. for 3.5 hours under 5 psi hydrogen pressure, the mixture was filtered, the catalyst was washed with ethanol. The combined filtrate was concentrated under reduced pressure to give crude 6-O-methylerythromycin A isopropylcyclohexyl ketal oxime as a glassy solid. The crude product was purified by column chromatography (100:2:1 chloroform: methanol: triethylamine) to give 205 mg of 6-O-methylerythromycin A 9-O-(2-chlorobenzyl) oxime as a white solid. The structure was confirmed by NMR and mass spectra. Mass spectrum (LC-MS): [M+H]+/z=887, MW=886. 1H NMR (500 MHz, $CDCl_3$); d (ppm)=1.42 (3H, s, 6-$CH_3$), 2.30 (6H, s, 3'-N—$(CH_3)_2$), 3.00 (3H, s, 6-$OCH_3$), 3.31 (3H,s,3"-$OCH_3$), 5.13 (2H, s, —$OCH_2$), 7.10~7.51 (4H, m, Ar). 13C NMR ($CDCl_3$); d (ppm) =40.3 (3'-N—$(CH_3)_2$), 49.4 (3"-$OCH_3$), 50.8 (6-$OCH_3$), 72.6 (-$OCH_2$), 78.7 (6-C), 96.0 (1"-C), 102.7 (1'-C), 126.5~135.7 (Ar-C), 171.0 (9-C), 175.5 (1-C).

Example 8

Preparation of 6-O-Methylerythromycin A Isopropylcyclohexyl Ketal Oxime

To a solution of 6-O-methylerythromycin A isopropylcyclohexyl ketal oxime N-oxide obtained above (92 mg) in isopropyl alcohol (5 ml) was added a solution of sodium bisulfide (200 mg) in $H_2O$ (1 ml). The reaction mixture was stirred at room temperate for 1 hours. The isopropyl alcohol was removed under reduced pressure. To the residue was added more $H_2O$ (10 ml), the white solid was suspended in $H_2O$ for 5 minutes, filtered and dried in the vacuum oven to give 84 mg of 6-O-methylerythromycin A isopropylcyclohexyl ketal oxime. The structure was confirmed by NMR and mass spectra. Mass spectrum (FAB): [M+H]+/z=903, MW=902. 1H NMR (500 MHz, $CDCl_3$); d (ppm)=1.41 (3H, s, 6-$CH_3$), 2.30 (6H, 3'-N—$(CH_3)_2$),3.11 (3H,6-$OCH_3$) 3.33 (3H, s, 3"-$OCH_3$). 13C NMR ($CDCl_3$); d (ppm)=40.3 (3'-N—$(CH_3)_2$), 49.4 (3"-$OCH_3$), 78.7 (6-C), 96.0 (1"-C), 102.7 (1'-C), 169.8 (9-C), 175.5 (1-C).

Example 9

Preparation of 6-O-Methylerythromycin A 9-O-(2-chlorobenzyl) Oxime

To a solution of 6-O-methylerythromycin A 9-O-(2-chlorobenzyl) oxime N-oxide obtained above (451 mg) in isopropyl alcohol (15 ml) was added a solution of sodium bisulfide (300 mg) in $H_2O$ (3 ml). The reaction mixture was stirred at room temperate for 30 minutes. The reaction mixture was poured into $H_2O$ , the product was extracted with ethyl acetate (2×50 ml), the organic layer were separated, combined, dried over $Na_2SO_4$ and concentrated under the reduced pressure to give 440 mg of 6-O-methylerythromycin A 9-O-(2-chlorobenzyl) oxime. The structure was confirmed by NMR and mass spectra. Mass spectrum (LC-MS): [M+H]+/z=887, MW=886. 1H NMR (500 MHz, $CDCl_3$); d (ppm)=1.42 (3H, s, 6-$CH_3$), 2.30 (6H, s, 3'-N—$(CH_3)_2$), 3.00 (3H, s, 6-$OCH_3$), 3.31 (3H, s, 3"-$OCH_3$), 5.13 (2H, s, -$OCH_2$), 7.10~7.51 (4H, m, Ar). 13C NMR ($CDCl_3$); d (ppm)=40.3 (3'-N—$(CH_3)_2$), 49.4 (3"-$OCH_3$), 50.8 (6-$OCH_3$), 72.6 (—$OCH_2$), 78.7 (6-C), 96.0 (1"-C), 102.7 (1'-C), 126.5~135.7 (Ar-C), 171.0 (9-C), 175.5 (1-C).

What is claimed is:

1. A compound having the formula:

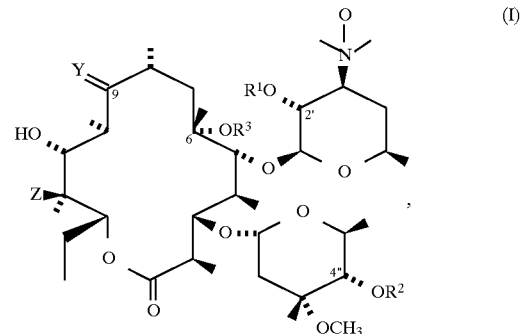

(I)

wherein $R^1$ and $R^2$ are independently hydrogen or a hydroxy-protecting group;

$R^3$ is a loweralkyl group;

Y is selected from the group consisting of:
a) an oxime having the formula N-O-$R^4$, wherein $R^4$ is selected from the group consisting of:
a loweralkenyl group;
an alkylaryl group;
substituted alkylaryl group;
an aryl(loweralkyl) group, or
a substituted aryl(loweralkyl) group; or b) an oxime having the formula:

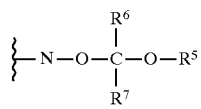

wherein
R$^5$ is selected from the group consisting of:
  a loweralkyl group,
  a cycloalkyl group,
  a phenyl group,
  an aryl(loweralkyl) group;
  or R$^5$ and R$^6$ or R$^5$ and R$^7$ and the atoms to which they are attached are taken together form a 5- to 7-membered ring containing one oxygen atom;
R$^6$ is selected from the group consisting of:
  a loweralkyl group,
  a loweralkoxymethyl group;
  or R$^6$ and R$^5$ and the atoms to which they are attached are taken together form a 5- to 7-membered ring containing one oxygen atom,
  or R$^7$ and R$^6$ and the atoms to which they are attached are taken together form a 5- to 7-membered cycloalkyl group; and
R$^7$ is selected from the group consisting of:
  a hydrogen atom,
  a loweralkyl group,
  a phenyl group,
  an aryl(loweralkyl) group;
  or R$^7$ and R$^5$ and the atoms to which they are attached are taken together form a 5- to 7-membered ring containing one oxygen atom;
  or R$^7$ and R$^6$ and the atoms to which they are attached are taken together form a 5- to 7-membered cycloalkyl group;
  with the requirement that only one pair of substituents (R$^5$ and R$^6$), (R$^5$ and R$^7$) or (R$^6$ and R$^7$) may be taken together with the atoms to which they are attached to form a ring as defined above; and
Z is hydrogen, hydroxy or protected-hydroxy.

2. The compound of claim 1, wherein R$^1$ and R$^2$ are both hydrogen.

3. The compound of claim 2, wherein R$^4$ is 2-chlorobenzyl.

4. The compound of claim 1, wherein the compound is 9-isopropylcyclohexyl ketal oxime, 3'-N-Oxide erythromycin A.

5. A process for preparing a compound of the formula:

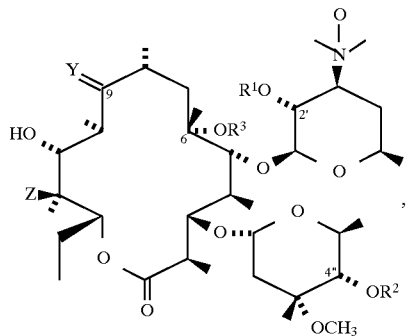

(I)

wherein R$^1$ and R$^2$ are independently hydrogen or a hydroxy-protecting group;
R$^3$ is a loweralkyl group;

Y is selected from the group consisting of:
  a) an oxime having the formula N-O-R$^4$, wherein R$^4$ is selected from the group consisting of:
    a loweralkenyl group;
    an alkylaryl group;
    substituted alkylaryl group;
    an aryl(loweralkyl) group, or
    a substituted aryl(loweralkyl) group; or
  b) an oxime having the formula:

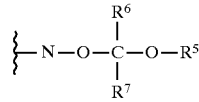

wherein
R$^5$ is selected from the group consisting of:
  a loweralkyl group,
  a cycloalkyl group,
  a phenyl group,
  an aryl(loweralkyl) group;
  or R$^5$ and R$^6$ or R$^5$ and R$^7$ and the atoms to which they are attached are taken together form a 5- to 7-membered ring containing one oxygen atom;
R$^6$ is selected from the group consisting of:
  a loweralkyl group,
  a loweralkoxymethyl group;
  or R$^6$ and R$^5$ and the atoms to which they are attached are taken together form a 5- to 7-membered ring containing one oxygen atom,
  or R$^7$ and R$^6$ and the atoms to which they are attached are taken together form a 5- to 7-membered cycloalkyl group; and
R$^7$ is selected from the group consisting of:
  a hydrogen atom,
  a loweralkyl group,
  a phenyl group,
  an aryl(loweralkyl) group;
  or R$^7$ and R$^5$ and the atoms to which they are attached are taken together form a 5- to 7-membered ring containing one oxygen atom;
  or R$^7$ and R$^6$ and the atoms to which they are attached are taken together form a 5- to 7-membered cycloalkyl group;
  with the requirement that only one pair of substituents (R$^5$ and R$^6$), (R$^5$ and R$^7$) or (R$^6$ and R$^7$) may be taken together with the atoms to which they are attached to form a ring as defined above; and
Z is hydrogen, hydroxy or protected-hydroxy. comprising the steps of:
  a) preparing a 9-O-protected oxime erythromycin derivative having the formula:

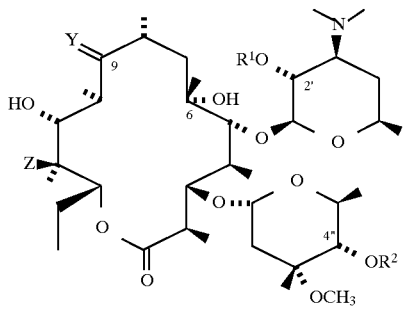

(II)

wherein Y, R$^1$, R$^2$, and Z are as defined above;

b) oxidizing the 3'-N of the 9-O-protected oxime erythromycin derivative to obtain a compound having the formula:

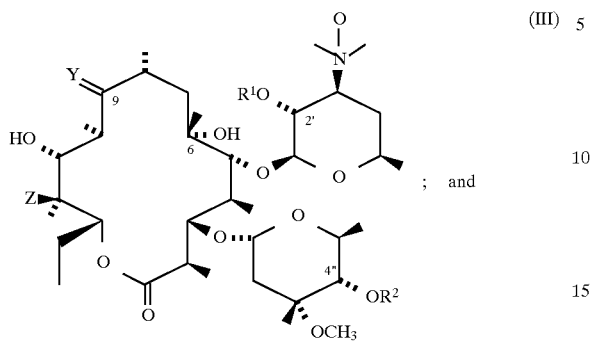

(III)

and c) alkylating the 6-hydroxy group of the compound of formula (II) with an alkylating agent.

6. The process of claim 5, wherein $R^1$ and $R^2$ are both hydrogen.

7. The process of claim 5, wherein $R^4$ is 2-chlorobenzyl.

8. The process of claim 5, wherein the compound is 9-isopropylcyclohexyl ketal oxime, 3'-N-Oxide erythromycin A.

9. The process of claim 5, wherein the oxidation is carried out by reacting the 9-O-protected oxime with a suitable oxidizing agent in a suitable solvent at a temperature from −20° C. to reflux temperature for a period of five minutes to 48 hours, and the alkylation is carried out with an alkylating agent in presence of a strong alkali metal base in a polar aprotic solvent at a reaction temperature for a period of time sufficient to effect alkylation.

10. The process of claim 9, wherein the alkylation is carried out with methyl iodide in the presence of potassium hydroxide at a temperature from about −15° C. to room temperature for a period of one to 8 hours.

11. The process of claim 10, wherein the compound is 9-isopropylcyclohexyl ketal oxime, 3'-N-Oxide erythromycin A.

12. A process of preparing 6-O-alkyl erythromycin A from a compound of formula:

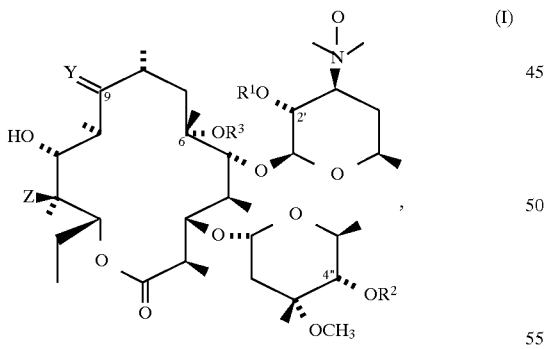

(I)

wherein $R^1$ and R2 are independently hydrogen or a hydroxy-protecting group;

$R^3$ is a loweralkyl group;

Y is selected from the group consisting of:
a) an oxime having the formula N-O-$R^4$, wherein $R^4$ is selected from the group consisting of:
a loweralkenyl group;
an alkylaryl group;
substituted alkylaryl group;
an aryl(loweralkyl) group, or
a substituted aryl(loweralkyl) group; or
b) an oxime having the formula:

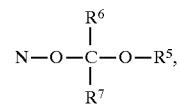

wherein $R^5$ is selected from the group consisting of:
a loweralkyl group,
a cycloalkyl group,
a phenyl group,
an aryl(loweralkyl) group;
or $R^5$ and $R^6$ or $R^5$ and $R^7$ and the atoms to which they are attached are taken together form a 5- to 7-membered ring containing one oxygen atom;

$R^6$ is selected from the group consisting of:
a loweralkyl group,
a loweralkoxymethyl group;
or $R^6$ and $R^5$ and the atoms to which they are attached are taken together form a 5- to 7-membered ring containing one oxygen atom,
or $R^5$ and $R^6$ and the atoms to which they are attached are taken together form a 5- to 7-membered cycloalkyl group; and $R^7$ is selected from the group consisting of:
a hydrogen atom,
a loweralkyl group,
a phenyl group,
an aryl(loweralkyl) group;
or $R^7$ and $R^5$ and the atoms to which they are attached are taken together form a 5- to 7-membered ring containing one oxygen atom;
or $R^7$ and $R^6$ and the atoms to which they are attached are taken together form a 5- to 7-membered cycloalkyl group;

with the requirement that only one pair of substituents ($R^5$ and $R^6$), ($R^5$ and $R^7$) or ($R^6$ and $R^7$) may be taken together with the atoms to which they are attached to form a ring as defined above; and Z is hydrogen, hydroxy or protected-hydroxy; comprising: eliminating 3'-N-oxide group, the 9-O-oxime protecting group, and optionally deprotecting the 2'- and 4"- hydroxy groups in the compounds.

* * * * *